(12) United States Patent
Dorenkamp et al.

(10) Patent No.: US 7,240,497 B2
(45) Date of Patent: Jul. 10, 2007

(54) CRYOSTAT HAVING A HEATING PLATE

(75) Inventors: Claudia Dorenkamp, Muehlhausen (DE); Stefan Kuenkel, Karlsruhe (DE)

(73) Assignee: Leica Microsystems Nussloch GmbH, Nussloch (DE)

( * ) Notice: Subject to any disclaimer, the term of this patent is extended or adjusted under 35 U.S.C. 154(b) by 306 days.

(21) Appl. No.: 10/986,681

(22) Filed: Nov. 12, 2004

(65) Prior Publication Data
US 2005/0109044 A1    May 26, 2005

(30) Foreign Application Priority Data
Nov. 22, 2003 (DE) ................ 203 18 094

(51) Int. Cl.
*F25B 19/00* (2006.01)
*F25C 5/02* (2006.01)
*H05B 1/00* (2006.01)
*H05B 3/00* (2006.01)
*A61B 18/18* (2006.01)
*B26D 5/00* (2006.01)

(52) U.S. Cl. .................... 62/51.1; 62/320; 219/201; 606/20; 83/367

(58) Field of Classification Search ............ 62/51.1, 62/320; 219/201; 606/20; 83/13, 367
See application file for complete search history.

(56) References Cited

U.S. PATENT DOCUMENTS

| | | | | |
|---|---|---|---|---|
| 3,733,948 A | * | 5/1973 | Pickett | 83/98 |
| 4,284,894 A | * | 8/1981 | Sitte et al. | 250/443.1 |
| 4,548,051 A | * | 10/1985 | Moessner | 62/320 |
| 4,979,376 A | | 12/1990 | Biehl et al. | |
| 5,048,300 A | * | 9/1991 | Lihl | 62/48.1 |
| 5,070,935 A | * | 12/1991 | Sitte et al. | 165/61 |
| 5,207,069 A | | 5/1993 | Matsuda et al. | |
| 5,761,977 A | * | 6/1998 | Jakobi et al. | 83/13 |
| 2001/0051365 A1 | * | 12/2001 | Morales et al. | 435/173.4 |
| 2002/0042147 A1 | * | 4/2002 | Ross et al. | 436/174 |
| 2004/0121485 A1 | * | 6/2004 | Hopkins et al. | 436/174 |
| 2005/0226770 A1 | * | 10/2005 | Allen et al. | 422/63 |

* cited by examiner

*Primary Examiner*—William C. Doerrler
(74) *Attorney, Agent, or Firm*—Hodgson Russ LLP

(57) ABSTRACT

A cryostat (1) having a sealable housing (2) is described, the housing (2) enclosing a coolable cryostat chamber (3). For cooling the cryostat chamber (3), a refrigeration device (4), a control system (5) and a power supply (6) are provided. For cutting frozen samples, a microtome is arranged in the cryostat chamber (3). A temperature-controllable heating plate (7) is integrated into the housing (2) of the cryostat (1), outside the cryostat chamber (3).

6 Claims, 1 Drawing Sheet

CRYOSTAT HAVING A HEATING PLATE

CROSS REFERENCE TO RELATED APPLICATIONS

This application claims priority of the German utility model application 203 18 094.1 filed Nov. 22, 2003 which is incorporated by reference herein.

FIELD OF THE INVENTION

The invention concerns a cryostat having a cryostat chamber in which a microtome for cutting frozen specimens is arranged.

BACKGROUND OF THE INVENTION

Such cryostats are used in order to cut frozen specimens with a microtome for subsequent viewing with a microscope. The preparations to be cut are cooled to a specific predefined temperature, the temperatures in this context generally being between −10° C. and −50° C. In order to achieve these temperatures, an appropriately dimensioned refrigeration device, with which a control system and a central power supply are associated, is provided in the cryostat.

To ensure a constant temperature, the microtomes are arranged in complexly encapsulated cryostat chambers, and the latter are correspondingly cooled with the refrigeration device.

The frozen specimens are cut using a microtome arranged in the cryostat chamber, and then transferred from the knife or knife holder onto a specimen slide. It has proven advantageous in this context if the specimen slides are temperature-controlled or preheated in order to ensure reliable transfer of the cut specimen. If the specimen slides are too cold, the section does not thaw out on the specimen slide, and the danger exists that there will be no adhesion and the section will then fall off.

Heating plates are available commercially, but they are always embodied as a separate unit, have a corresponding space requirement, and must be arranged separately from the cryostat.

SUMMARY OF THE INVENTION

It is therefore the object of the present invention to improve the arrangement of the heating plate and thus guarantee ergonomic operation.

This object is achieved, according to the present invention, by way of a temperature-controllable heating plate integrated into the housing of the cryostat but outside the cryostat chamber. This guarantees that the heating plate is freely accessible when working at the cryostat, thus making work at the cryostat more ergonomic.

In an embodiment of the invention, the heating plate is electrically connected to the control system and/or to the power supply. The result of this is that the existing electrical devices can also be used by the heating plate, and complex additional control systems and/or power supplies can be omitted.

In a refinement of the invention, a temperature sensor that is electrically connected to the control system is associated with the heating plate. The result of this is that a predefined temperature is maintained in constant fashion at the heating plate.

In a refinement of the invention, the heating plate is arranged in the housing of the cryostat at lectern height (approx. 110 cm high). The result, in ergonomically favorable fashion, is that the specimen slides with the cut sections that are placed on the heating plate can be written on.

In a further embodiment of the invention, a setting unit for adjusting the temperature of the heating plate is associated with the control system. The result of this is that the heating plate temperature can be influenced not only by parameters permanently set at the control system, but only or additionally by way of a manual definition.

BRIEF DESCRIPTION OF THE DRAWING

The invention will be explained in more detail with reference to FIG. 1, which shows, in schematic fashion, a cryostat formed in accordance with an exemplary embodiment of the present invention.

DETAILED DESCRIPTION OF THE INVENTION

Figure 1:
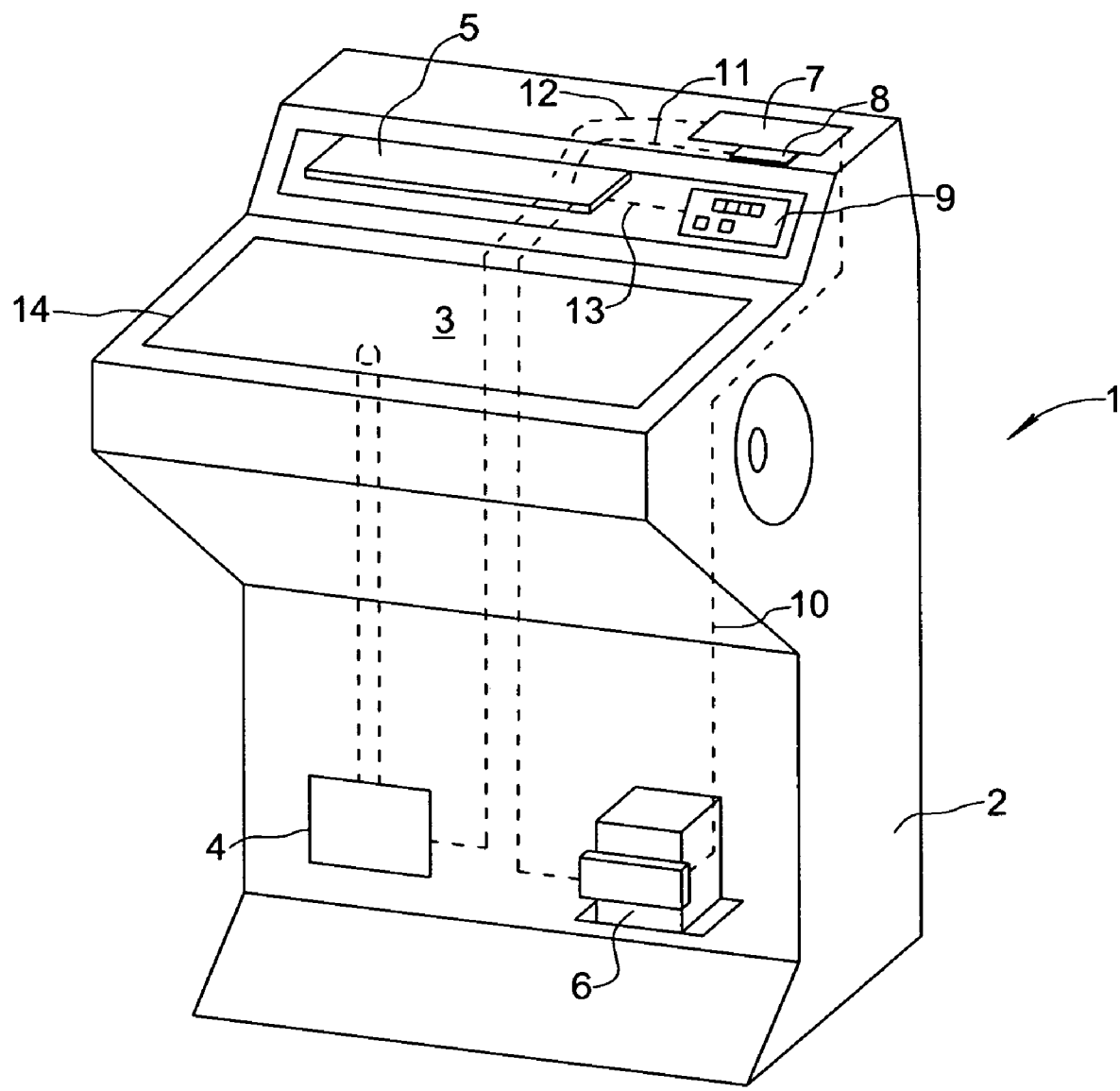

FIG. 1 is a view of a cryostat 1 having a housing 2 that encloses a cryostat chamber 3 in which a microtome (not depicted) is arranged. Cryostat chamber 3 is accessible to the user via a cover 14. A refrigeration device 4 is provided to cool cryostat chamber 3. A control system 5 and a central power supply 6 are arranged in housing 2 for the operation of cryostat 1. A heating plate 7 for temperature control and placement of specimen slides is integrated into housing 2 of cryostat 1. Heating plate 7 is connected via a first electrical connection 10 to the central power supply, and via a second electrical connection 12 to control system 5. A temperature sensor 8 for measuring the heating plate temperature is furthermore integrated into housing 2, and connected via an electrical connection 11 to control system 5. A setting unit 9, which is connected via an electrical connection 13 to control system 5, is provided for manual definition of a specific temperature of heating plate 7.

The desired temperature at heating plate 7 is preselected via setting unit 9. By way of control system 5, current is applied to the heating plate until the preselected temperature is measured by temperature sensor 8. The delivery of current to heating plate 7 is thus shut off by way of control system 5. When a lower temperature of heating plate 7 is measured by temperature sensor 8, the interruption in current delivery is canceled again.

Heating plate 7 is arranged in housing 2 of cryostat 1 at normal lectern height, i.e. approx. 110 cm, so that the specimen slides placed on heating plate 7 can be written on at an ergonomically favorable working height. In a preferred embodiment of the invention, the heating plate is sized to accommodate at least three standard glass specimen slides each measuring 25 mm×75 mm. This ensures not only that the specimen slide can be preheated before receiving the cut specimen, but also that the specimen slide together with the specimen can additionally be placed on the heating plate for specimen drying.

PARTS LIST

1 Cryostat
2 Housing
3 Cryostat chamber
4 Refrigeration device
5 Control system
6 Power supply
7 Heating plate
8 Temperature sensor
9 Setting unit 10 Electrical connection 6-7
11 Electrical connection 5-8
12 Electrical connection 5-7
13 Electrical connection 5-9
14 Cover

What is claimed is:

1. A cryostat for containing a microtome in a temperature-controlled environment, the cryostat comprising:
    a housing enclosing a cryostat chamber;
    a refrigeration device communicating with the cryostat chamber for cooling the cryostat chamber;
    a control system electrically connected to the refrigeration device;
    a power supply electrically connected to the control system; and
    a temperature controllable heating plate integrated into the housing outside the cryostat chamber.

2. The cryostat as defined in claim 1, wherein the heating plate is electrically connected to the control system.

3. The cryostat as defined in claim 2, further comprising a temperature sensor associated with the heating plate and electrically connected to the control system.

4. The cryostat as defined in claim 1, wherein the heating plate is sized to accommodate at least three standard specimen slides measuring 25 mm×75 mm.

5. The cryostat as defined in claim 1, further comprising a setting unit electrically connected to the control system for enabling a user to input a desired temperature of the heating plate to the control system.

6. The cryostat as defined in claim 1, wherein the heating plate is integrated into the housing of the cryostat at lectern height or at substantially lectern height.

* * * * *